(12) United States Patent
Lai et al.

(10) Patent No.: US 9,585,734 B2
(45) Date of Patent: Mar. 7, 2017

(54) LOW PROFILE SELF-LIGATING ORTHODONTIC APPLIANCE WITH CLIP

(75) Inventors: Ming-Lai Lai, Arcadia, CA (US);
Calvin N. Corpus, Brea, CA (US);
Ruedger Rubbert, Berlin (DE);
Hans-Christian Krueger, Berlin (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 331 days.

(21) Appl. No.: 13/056,171

(22) PCT Filed: Jul. 27, 2009
(Under 37 CFR 1.47)

(86) PCT No.: PCT/US2009/051790
§ 371 (c)(1),
(2), (4) Date: Aug. 27, 2013

(87) PCT Pub. No.: WO2010/014518
PCT Pub. Date: Feb. 4, 2010

(65) Prior Publication Data
US 2014/0065566 A1 Mar. 6, 2014

Related U.S. Application Data

(60) Provisional application No. 61/084,691, filed on Jul. 30, 2008.

(51) Int. Cl.
*A61C 7/30* (2006.01)
*A61C 7/14* (2006.01)

(52) U.S. Cl.
CPC .............. *A61C 7/30* (2013.01); *A61C 7/145* (2013.01); *Y10T 29/49568* (2015.01)

(58) Field of Classification Search
CPC ............ A61C 7/30; A61C 7/145; A61C 7/287
(Continued)

(56) References Cited

U.S. PATENT DOCUMENTS

| 1,991,047 A | 2/1935 | Edward |
| 2,368,851 A | 2/1945 | Laskin |

(Continued)

FOREIGN PATENT DOCUMENTS

| EP | 1234549 | 8/2002 |
| EP | 1235528 | 10/2002 |

(Continued)

OTHER PUBLICATIONS

Voudouris, "Seven Clinical Principles of Interactive Twin Mechanisms", Journal Clinical Orthodontics, Inc. 1997, vol. XXXI, No. 1, pp. 55-65.

(Continued)

*Primary Examiner* — Edward Moran (57) ABSTRACT

An orthodontic appliance includes a body (16) and at least one clip (36) connected to the body for retaining an archwire in an archwire slot (18). The body and each clip have matching, generally oval-shaped external profiles that present a compact, low-profile configuration. Each clip includes at least one prong (46) that engages a tab for helping to retain the clip in connected relationship to the body. Each tab is connected to the body by a protrusion that has a top surface coplanar with a bottom wall of the archwire slot.

17 Claims, 7 Drawing Sheets

(58) Field of Classification Search
USPC .......................................................... 433/11
See application file for complete search history.

(56) References Cited

U.S. PATENT DOCUMENTS

| | | | |
|---|---|---|---|
| 3,052,027 A | | 9/1962 | Wallshein |
| 3,084,437 A | | 4/1963 | Neger |
| 3,327,393 A | | 6/1967 | Brader |
| 3,464,112 A | | 9/1969 | Silverman |
| 3,464,113 A | | 9/1969 | Silverman |
| 3,724,074 A | | 4/1973 | Wallshein |
| 3,772,787 A | | 11/1973 | Hanson |
| 4,023,274 A | * | 5/1977 | Wallshein ............... A61C 7/30 433/11 |
| 4,103,423 A | | 8/1978 | Kessel |
| 4,149,314 A | | 4/1979 | Nonnenmann |
| 4,171,568 A | | 10/1979 | Forster |
| 4,197,642 A | | 4/1980 | Wallshein |
| 4,248,588 A | | 2/1981 | Hanson |
| 4,260,375 A | | 4/1981 | Wallshein |
| 4,371,337 A | | 2/1983 | Pletcher |
| 4,492,573 A | | 1/1985 | Hanson |
| 4,496,318 A | | 1/1985 | Connelly |
| 4,531,911 A | | 7/1985 | Creekmore |
| 4,551,094 A | | 11/1985 | Kesling |
| 4,559,012 A | | 12/1985 | Pletcher |
| 4,698,017 A | | 10/1987 | Hanson |
| 4,712,999 A | | 12/1987 | Rosenberg |
| 4,725,229 A | | 2/1988 | Miller |
| 4,846,681 A | | 7/1989 | Mourany |
| 5,039,302 A | | 8/1991 | Keys |
| 5,094,614 A | | 3/1992 | Wildman |
| 5,174,754 A | | 12/1992 | Meritt |
| 5,269,681 A | | 12/1993 | Degnan |
| 5,322,435 A | | 6/1994 | Pletcher |
| 5,356,289 A | | 10/1994 | Watanabe |
| 5,358,402 A | | 10/1994 | Reed |
| 5,366,372 A | | 11/1994 | Hansen |
| 5,380,196 A | | 1/1995 | Kelly |
| 5,439,379 A | | 8/1995 | Hansen |
| 5,466,151 A | | 11/1995 | Damon |
| 5,474,445 A | | 12/1995 | Voudouris |
| 5,516,284 A | | 5/1996 | Wildman |
| 5,562,444 A | | 10/1996 | Heiser |
| 5,613,850 A | | 3/1997 | Wildman |
| 5,630,715 A | | 5/1997 | Voudouris |
| 5,630,716 A | | 5/1997 | Hanson |
| 5,685,711 A | | 11/1997 | Hanson |
| 5,711,666 A | | 1/1998 | Hanson |
| 5,857,849 A | | 1/1999 | Kurz |
| 5,857,850 A | | 1/1999 | Voudouris |
| 5,863,199 A | | 1/1999 | Wildman |
| 5,890,893 A | | 4/1999 | Heiser |
| 5,908,293 A | | 6/1999 | Voudouris |
| 5,913,680 A | | 6/1999 | Voudouris |
| 5,967,773 A | | 10/1999 | Roman |
| 5,971,753 A | | 10/1999 | Heiser |
| 6,071,119 A | | 6/2000 | Christoff |
| 6,168,428 B1 | | 1/2001 | Voudouris |
| 6,193,508 B1 | | 2/2001 | Georgakis |
| 6,302,688 B1 | | 10/2001 | Jordan |
| 6,554,612 B2 | * | 4/2003 | Georgakis ............... A61C 7/30 433/11 |
| 6,582,226 B2 | | 6/2003 | Jordan |
| 6,733,285 B2 | | 5/2004 | Puttler |
| 6,776,614 B2 | | 8/2004 | Wiechmann |
| 6,957,957 B2 | | 10/2005 | Pospisil |
| 7,140,876 B2 | * | 11/2006 | Cinader ............... A61C 7/30 433/10 |
| 7,217,125 B2 | | 5/2007 | Lai |
| 7,377,777 B2 | | 5/2008 | Lai |
| 2003/0118967 A1 | | 6/2003 | Tepper |
| 2003/0152884 A1 | * | 8/2003 | Wiechmann et al. ............ 433/9 |
| 2004/0072118 A1 | | 4/2004 | Heiser |
| 2004/0086826 A1 | * | 5/2004 | Pospisil ............... 433/11 |
| 2007/0148610 A1 | | 6/2007 | Lai |
| 2007/0178423 A1 | | 8/2007 | Rubbert |

FOREIGN PATENT DOCUMENTS

| | | |
|---|---|---|
| EP | 1458303 | 6/2007 |
| JP | 58-50951 | 3/1983 |
| JP | 59-16612 | 2/1984 |
| JP | 1-165015 | 11/1989 |
| JP | H06-26814 | 4/1994 |
| WO | 98-20805 | 5/1998 |
| WO | 01-22901 | 4/2001 |
| WO | 02-089693 | 11/2002 |
| WO | 2005-044131 | 5/2005 |
| WO | 2007-085656 | 8/2007 |
| WO | WO 2007/141226 | 12/2007 |
| WO | 2010-014299 | 2/2010 |

OTHER PUBLICATIONS

International Search Report for PCT/US2009/051790, mailed Jul. 8, 2010, 7 pages.

* cited by examiner

LOW PROFILE SELF-LIGATING ORTHODONTIC APPLIANCE WITH CLIP

CROSS REFERENCE TO RELATED APPLICATIONS

This application is a national stage filing under 35 U.S.C. 371 of PCT/US2009/051790, filed Jul. 27, 2009, which claims priority to U.S. Application No. 61/084,691, filed Jul. 30, 2008, the disclosure of which is incorporated by reference in its/their entirety herein.

BACKGROUND OF THE INVENTION

1. Field of the Invention

This invention broadly relates to intra-oral appliances that are used during the course of orthodontic treatment. More particularly, the present invention relates to self-ligating orthodontic appliances having one or more clips for releasably retaining an archwire in an archwire slot of the appliance.

2. Description of the Related Art

Orthodontic therapy is a specialized type of treatment within the field of dentistry, and involves of repositioning of malpositioned teeth to orthodontically correct locations. Orthodontic therapy often enhances the aesthetic appearance of the teeth, especially in instances when the patient's front teeth are malpositioned or crooked. Orthodontic treatment can also improve the patient's occlusion so that opposed teeth function better with each other during the times that the patient is chewing.

Many types of orthodontic treatment programs involve the use of a set of tiny appliances and archwires that are commonly known collectively as "braces". During such treatment programs, small appliances known as brackets are fixed to the patient's anterior, cuspid and bicuspid teeth, and an archwire is inserted into a slot of each bracket. The archwire forms a track to guide movement of the teeth to desired positions. End sections of the archwires are often captured in tiny appliances known as buccal tubes that are fixed to the patient's molar teeth.

Many orthodontic brackets have small wings known as "tiewings" that are connected to a body of the bracket. Once the bracket has been attached to a tooth and an archwire has been placed in the archwire slot of the bracket, a ligature is coupled to the bracket in order to retain the archwire in the archwire slot. One example of a commercially available orthodontic ligature is a small, elastomeric O-ring that is installed by stretching the O-ring along a path behind the tiewings and over the facial side of the archwire.

Other types of orthodontic appliances are known as self-ligating brackets, and are provided with a latch for coupling the archwire to the bracket. Use of the latch avoids the need to use a ligature to secure the archwire to the bracket. The latch may comprise a movable clip, spring member, sliding cover, shutter, bail or other structure that is connected to the bracket body for retaining the archwire in the archwire slot.

Examples of improved, self-ligating orthodontic appliances with clips are described in applicant's U.S. Pat. Nos. 6,582,226, 7,140,876, and 7,217,125 and 7,377,777. The appliances described in those documents have one or more clips for retaining an archwire in the archwire slot, and the clips release the archwire from the archwire slot whenever the archwire exerts a force on the appliance that exceeds a certain minimum value. The minimum value is significantly less than the force required in the same direction to debond the appliance from the tooth, and consequently helps to ensure that the appliance will not spontaneously debond from the tooth during the course of treatment.

U.S. Pat. No. 6,776,614 describes a system of customized orthodontic brackets and archwires. This patent further describes designing the brackets on a computer as a combination of three-dimensional virtual objects including a virtual bracket bonding pad and a virtual bracket body retrieved from a library of virtual bracket bodies. The virtual brackets can be represented as a file containing digital shape data that can be exported to a rapid prototype fabrication device. The rapid prototype fabrication device can be used to make models of the brackets which, in turn, are then used to form molds for subsequent casting of the brackets.

Orthodontic appliances including brackets having an overall, generally small or low profile are often desired by practitioners for use in treatment. Such low profile appliances are less likely to contact other teeth or appliances in the patient's oral cavity, an important advantage in certain instances when the teeth are not initially positioned in substantial alignment relative to each other. Low profile appliances are also less likely to impinge on the patient's oral tissue and cause irritation of the same.

SUMMARY OF THE INVENTION

The present invention is directed toward improvements in low profile orthodontic appliances, including low profile self-ligating appliances that include one or more clips. The appliances present an overall external profile that is relatively small and comfortable, a significant benefit when the appliances are used on the lingual side of the patient's teeth. The low profile appliances are also less likely to irritate adjacent oral tissue or come into contact with teeth or other appliances located in the patient's oral cavity.

In more detail, the present invention in one aspect is directed to a self-ligating orthodontic appliance that comprises a base having an outer surface for bonding to a tooth and a neck extending outwardly from the base. A body is connected to the neck and includes an elongated archwire slot extending in a generally mesial-distal direction with two sidewalls and a bottom wall. The body presents a generally oval-shaped or generally teardrop-shaped external profile when viewed in directions along the longitudinal axis of the archwire slot. The appliance also includes at least one clip connected to the body for ligating an orthodontic archwire in the archwire slot. Each clip presents a generally oval-shaped or generally teardrop-shaped external profile that matches and is aligned with the external profile of the body.

The present invention in another aspect is directed to a custom, self-ligating orthodontic appliance that comprises a base having a configuration matching the configuration of a specific tooth of a specific patient. The appliance also includes a body integrally connected to the base, the body including an elongated archwire slot extending in a generally mesial-distal direction. The appliance additionally includes a latch coupled to the body for releasably retaining an archwire in the archwire slot, wherein the latch and the body comprising initially separate, discrete components. The archwire slot and the latch of the appliance together form an assembly, and the assembly has a certain orientation relative to the base that is customized to the configuration of the specific tooth of the specific patient.

The present invention is also directed in another aspect to a method of making an orthodontic brace. This method comprises:

for each tooth to receive an appliance, defining an appliance base having a configuration that matches the configuration of a specific tooth of a specific patient;

for each appliance, forming the appliance base together with an appliance body as an integral component, the body including an archwire slot having a certain orientation relative to the base that is selected according to the specific tooth configuration of the specific patient; and for each appliance, connecting a latch to the body for releasably retaining an archwire in the archwire slot, wherein the act of connecting the latch to the body includes the act of positioning the latch at a certain orientation relative to the archwire slot, and wherein the certain orientation is relatively constant for each appliance of the brace.

Another aspect of the invention is directed to a self-ligating orthodontic appliance that comprises a base and a body connected to the base. The body includes an elongated archwire slot that extends in a generally mesial-distal direction. A protrusion extends outwardly from the body adjacent the archwire slot. The protrusion includes a top surface. The appliance also includes a clip connected to the protrusion, and the clip includes a region next to the archwire slot for receiving an archwire. The clip includes arm portions next to the region that are movable away from each other in order to admit an archwire into the archwire receiving region. The clip also includes a recess that receives the protrusion and a prong extending between the recess and the archwire-receiving region. The prong extends across the top surface of the protrusion, and the protrusion includes a tab that is located next to the prong. The tab extends in a direction toward the archwire receiving region in order to help retain the clip in connected relationship with the protrusion.

Another aspect of the invention is directed toward a method of making a self-ligating orthodontic appliance having at least one ligating clip. This method comprises:

constructing an appliance preform that includes a body and at least one protrusion extending outwardly from the body in a direction generally along a mesial-distal reference axis;

advancing a cutting tool into the preform in order to cut an archwire slot having two sidewalls and a bottom wall in the body, wherein the act of advancing the cutting tool into the preform also includes the act of cutting a portion of the protrusion in order to form a top surface of the protrusion that is coplanar with the bottom wall of the archwire slot.

Further details of the invention are defined in the features of the claims.

DEFINITIONS

As used herein, and with respect to a location along the patient's curved dental arch:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION OF THE PREFERRED EMBODIMENTS

An orthodontic appliance that is constructed in accordance with one embodiment of the present invention is illustrated in FIGS. 1-4 and is broadly designated by the numeral 10. In this embodiment, the appliance 10 is an orthodontic bracket that is adapted to be secured to a lingual surface of a patient's non-molar tooth. Alternatively, however, the appliance could be a lingual molar appliance, a facial (labial) molar appliance, a facial non-molar appliance or any other orthodontic appliance that is adapted to receive an archwire for controlling movement of the associated tooth during the course of orthodontic treatment.

The appliance 10 includes a base for bonding the appliance 10 directly to the patient's tooth enamel by the use of an adhesive. Preferably, and as shown in the drawings, the base 12 has an outer, tooth-facing surface with a compound contour that matches the compound contour of the patient's tooth surface. As one embodiment, the compound contour of the outer tooth-facing surface is custom-made to precisely mate with the enamel surface of the patient's tooth in close-fitting relation. Optionally, the tooth-facing surface of the base 12 may be provided with grooves, particles, recesses, undercuts, a chemical bond enhancement material or any other material or structure or any combination of the foregoing that enhances the resulting bond between the appliance 10 and the patient's tooth enamel.

As one alternative, the shape of the outer, tooth-facing surface of the base 12 can be derived directly from digital representations of the patient's tooth so as to produce a bonding surface that precisely conforms to the shape of the tooth surface. According to one methodology described in U.S. Pat. No. 6,776,614 (Wiechmann et al.), a software algorithm is employed that automatically or semi-automatically calculates an appropriate bracket bonding pad area by analyzing the curvature of the tooth surface and determines a base surface that is large enough to cover substantial curvature features to allow for reliable manual positioning of the appliance 10 onto the tooth surface. For a lingual appliance, such an algorithm could for instance start with a pre-defined pad size, wherein the tooth surface covered by that pad size would form a virtual "knoll" having at least one raised portion relative to surrounding tooth anatomy, since a completely flat tooth surface would not lend itself to unique positioning of an appliance. The volume of the knoll could be calculated provided that the edges of the base 12 are joined by a continuous surface in any convenient manner. The less curvature the tooth surface presents, the flatter the knoll and the smaller its volume would be. If the volume of the knoll does not exceed a pre-defined value, the volume of the base 12 would automatically be enlarged by a pre-defined value, with the idea that the larger volume would be more likely to include adequate raised tooth features. Again, the volume would be calculated. This loop would be continued until a minimum value for the volume would be achieved for the base 12. Alternative methods of determining the shape of the base 12 are also possible.

A neck 14 of the appliance 10 extends outwardly from the base 12, and optionally extends in a direction generally parallel to the occlusal plane of the patient when the appliance is bonded to the patient's tooth. A lingual portion of the neck 14 is fixedly connected to a body 16. Optionally, and as shown in the drawings, the body 16 has an overall height in an occlusal-gingival direction that is greater than the overall height of the neck 14 in the same direction when viewed in reference planes perpendicular to the direction of extension of the neck 14 away from the base 12. Optionally, the body 16 also has an overall width in a mesial-distal direction that is greater than the mesial-distal width of the neck 14 when considered in the same reference planes.

The body 16 includes an elongated archwire slot 18 that extends in a generally mesial-distal direction. The archwire slot 18 includes two sidewalls 20, 22 that are parallel to each other as well as a bottom wall 24 that extends between the two sidewalls 20, 22 in a generally perpendicular relation. When viewed in directions along the longitudinal axis of the archwire slot 18, the sidewalls 20, 22 and the bottom wall 24, together present a generally "U"-shaped configuration that is adapted to matingly receive an archwire having a generally rectangular cross-sectional configuration.

Preferably, the archwire slot 18 is oriented so that an archwire is received in the archwire slots of all appliances located on the dental arch, including the archwire slot 18 of the appliance 10, by moving the archwire toward the arch in a direction perpendicular to the occlusal plane of the patient. To this end, the bottom wall 24 is preferably parallel to this occlusal plane and the sidewalls 20, 22 are preferably perpendicular to the bottom wall 24. Such orientations facilitate insertion of the archwire into all of the archwire slots simultaneously without undue bending of the archwire.

The appliance 10 also includes a mesial protrusion 26 that extends outwardly from the body 16 in a generally mesial direction, and a distal protrusion 28 that extends outwardly from the body 16 in a generally distal direction. The protrusions 26, 28 each have a flat top surface 30 that is coplanar with the flat bottom wall 24 of the archwire slot 18. Optionally, and in the embodiment shown in the drawings, the protrusions 26, 28 also include generally flat, external lingual and facial wall portions that are each connected by respective curved corner surfaces to a generally flat gingival wall portion.

Each of the protrusions 26, 28 includes an outer end portion having a pair of tabs 32 that are spaced apart from each other. Each tab 32 extends away from the top surface 30 in a generally occlusal direction that is generally parallel to the direction of extension of the sidewalls 20, 22 away from the bottom wall 24 of the archwire slot 18. Preferably, the facing, inner surfaces of the tabs 32 of the protrusions 26, 28 are coplanar with aligned regions of the respective sidewalls 20, 22.

The appliance 10 additionally includes a latch for releasably retaining an orthodontic archwire in the archwire slot 18. In the embodiment shown in FIGS. 1-4, the latch comprises a mesial ligating clip 34 and a distal ligating clip 36. The mesial clip 34 is shown alone in FIG. 6 in side elevational view. Optionally, the distal clip 36 is identical in construction to the mesial clip 34.

Figure 1:
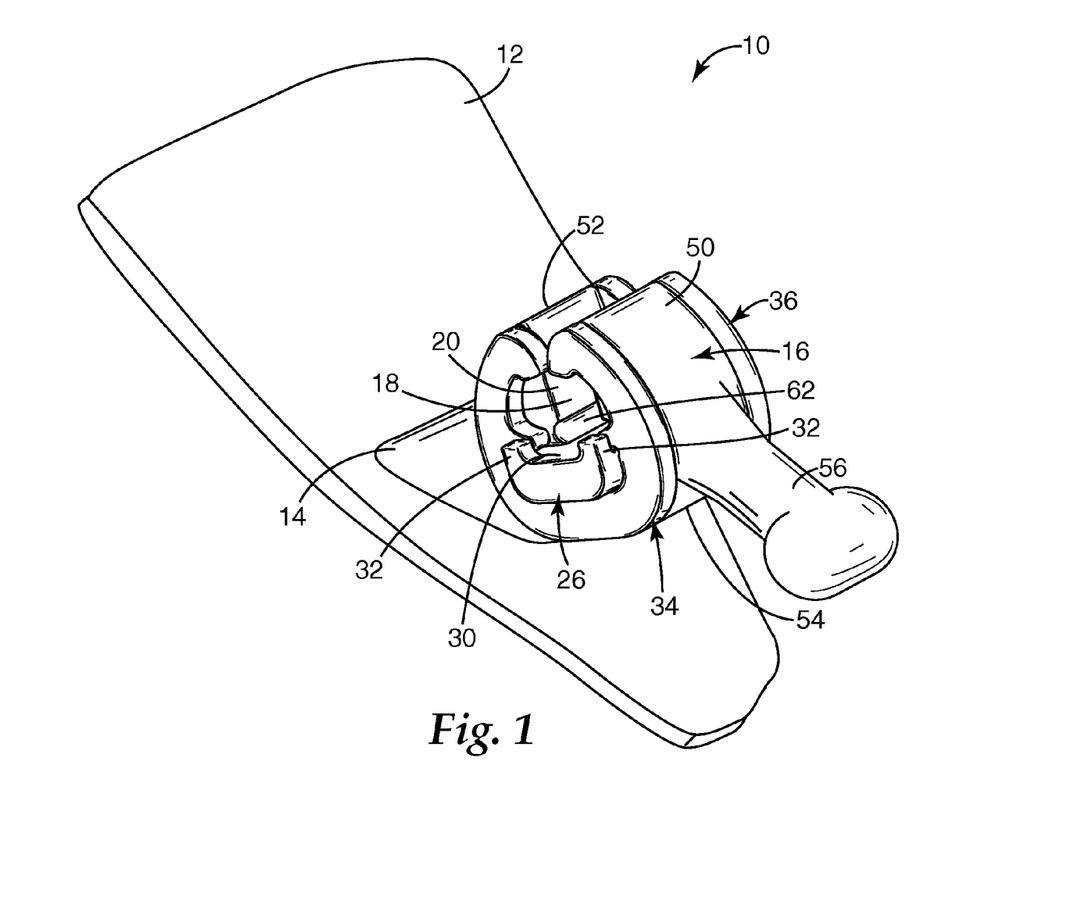
FIG. 1 is a perspective view of a self-ligating orthodontic appliance that is constructed in accordance with one embodiment of the present invention, looking at the appliance in a direction toward its mesial, lingual and occlusal sides.
Figure 2:
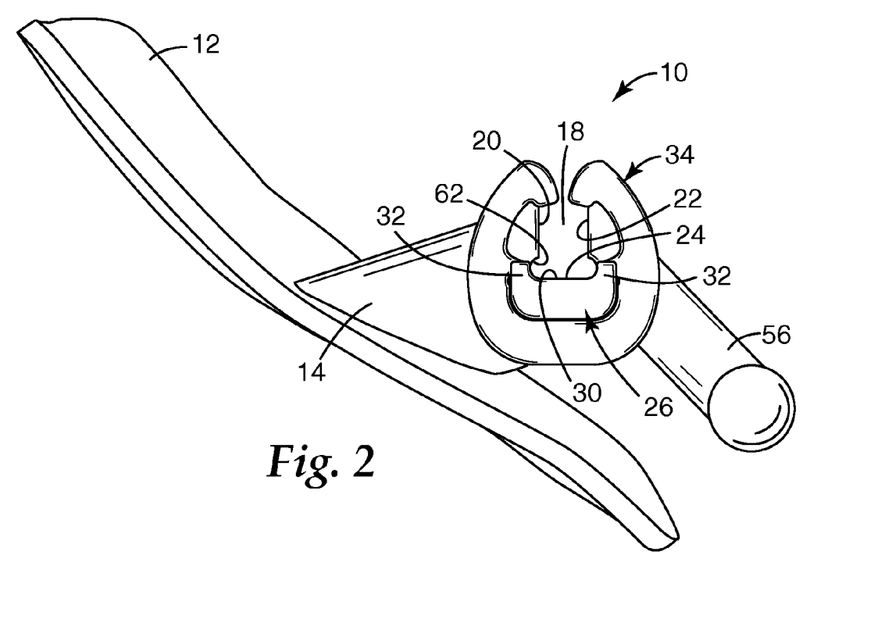
FIG. 2 is a side elevational view of the appliance shown in FIG. 1, looking in a direction directly toward the mesial side of the appliance and aligned with the longitudinal axis of an archwire slot of the appliance.
Figure 3:
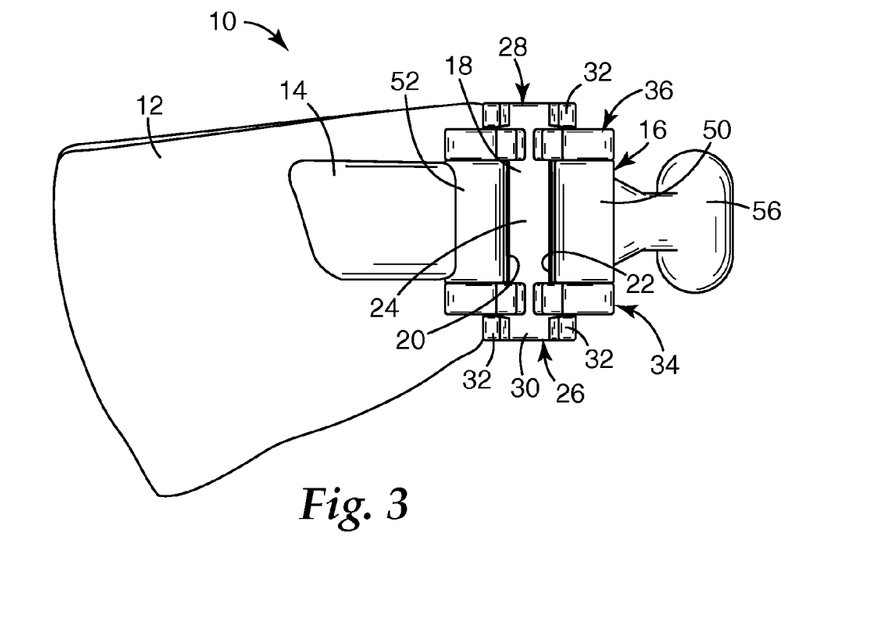
FIG. 3 is another perspective view of the orthodontic appliance shown in FIGS. 1 and 2, looking at the appliance in a direction toward its mesial, lingual and occlusal sides.
Figure 4:
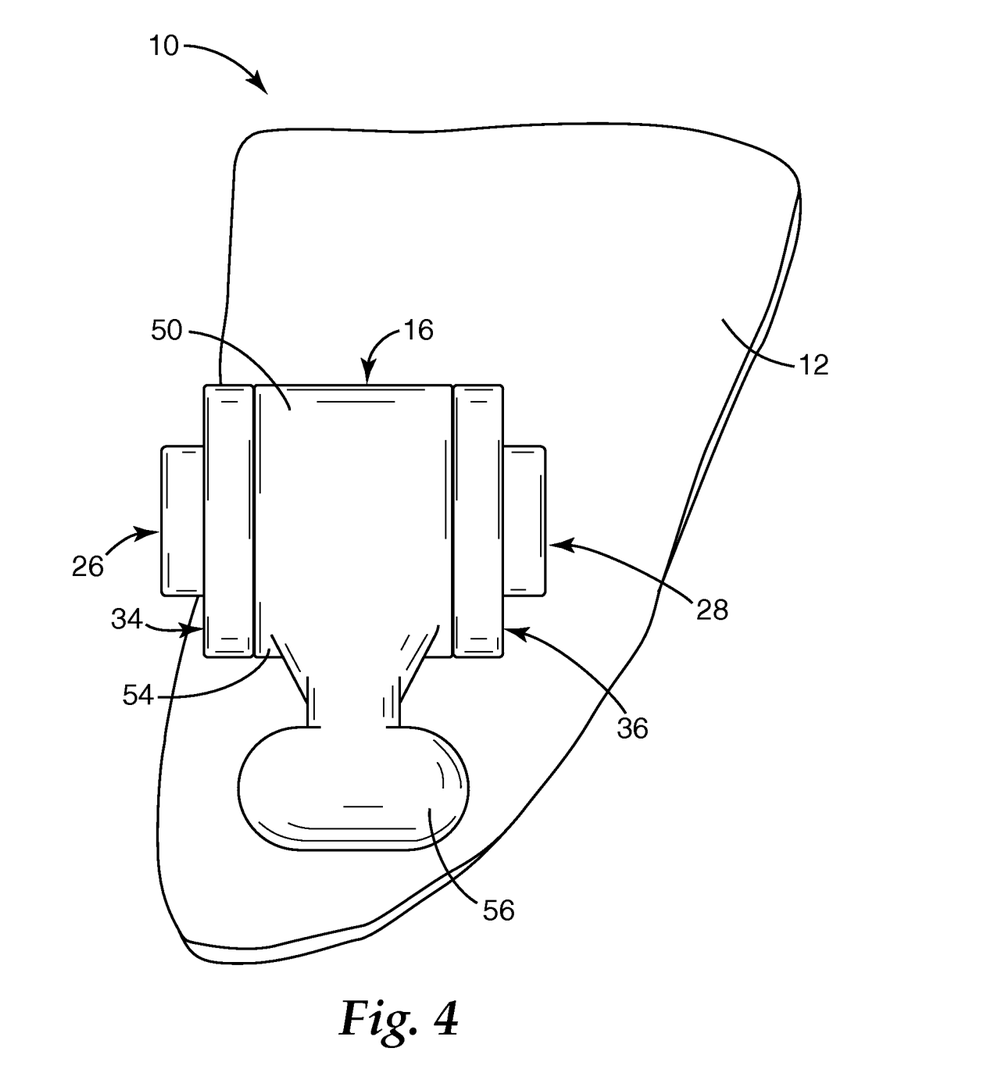
FIG. 4 is yet another perspective view of the orthodontic appliance shown in FIGS. 1 and 3, looking at the appliance in a direction toward its distal and gingival sides.
Figure 5:
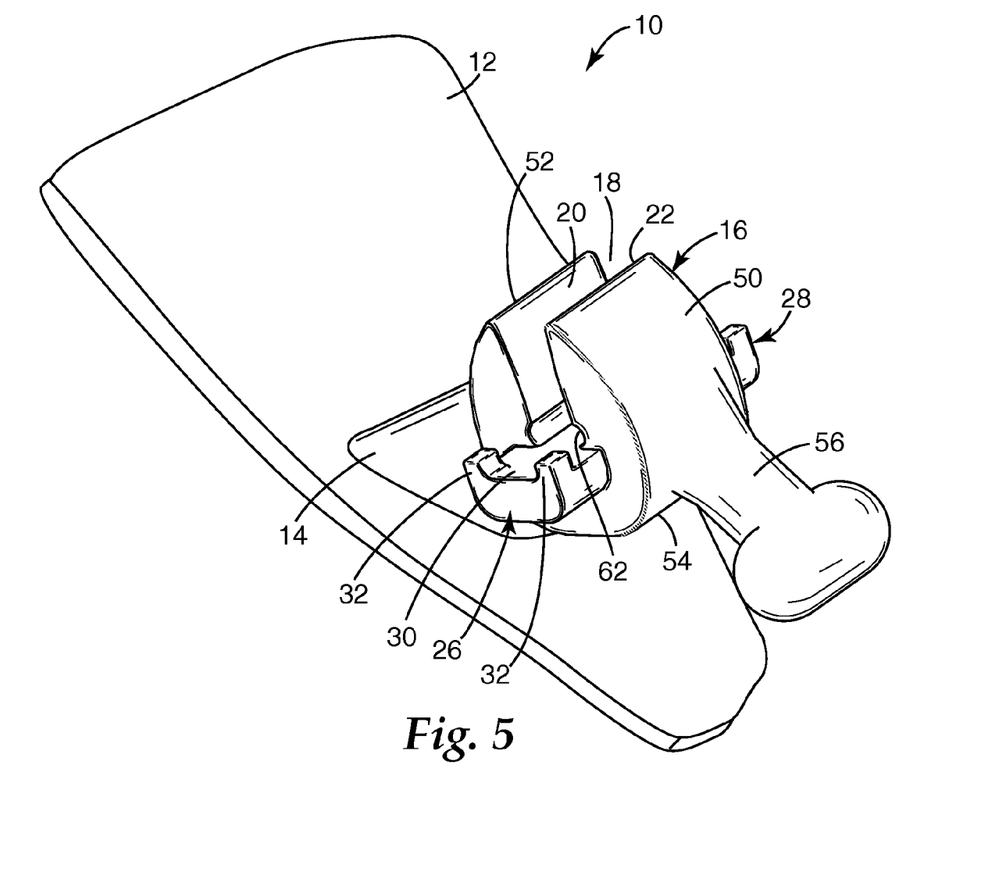
FIG. 5 is a view somewhat similar to FIG. 1 except that ligating clips of the appliance have been omitted.
Figure 6:
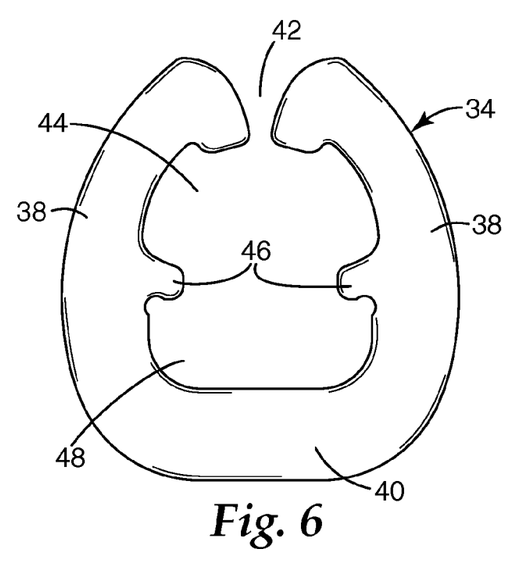
FIG. 6 is a side elevational view of one of the ligating clips of the appliance illustrated in FIGS. 1-4.

As shown for example in FIG. 6, the mesial clip 34 includes two elongated, curved arm portions 38 that are integrally connected to a bottom portion 40. The outer edges of the arm portions 38 and the outer edge of the bottom portion 40 together present a generally oval-shaped configuration. Optionally, the outer edge of the bottom portion 40 is somewhat flattened. Outer ends of the arm portions 38 remote from the bottom portion 40 are inclined in directions toward each other and present an opening 42.

The clip 34 includes an archwire-receiving region 44 (FIG. 6) adjacent the opening 42 and a recess 48 for receiving the mesial protrusion 26 when the clip 34 is assembled to the body 16 as shown in FIGS. 1-4. The clip 34 also includes a pair of prongs 46 that are each connected to a mid-portion of a respective arm portion 38. The prongs 46 extend between the archwire-receiving region 44 and the recess 48 and in directions toward each other. Each prong 46 also has a small undercut that faces the recess 48.

The clip 34 is shown in its normal, relaxed orientation in the drawings. However, the arm portions 38 are movable away from each other when desired in order to open the clip 34 and admit an archwire into the archwire-receiving region 44. The adjacent, outer end sections of the arm portions 38 are inclined in directions toward each other as the archwire-receiving 44 is approached, which helps to deflect the arm portions 38 away from each other as the archwire is moved into the region 44.

The prongs 46 slide across the top surface 30 of the mesial protrusion 26 as the clip 34 is opened. However, the prongs 46 extend inwardly and toward each other a distance sufficient to remain in contact with the top surface 30 when the clip 34 is opened to an extent sufficient to receive an archwire. As such, the clip 34 remains coupled to the protrusion 26 during such opening movements and the prongs 46 essentially preclude movement of the clip 34 in a gingival direction, which might otherwise enable the clip 34 to detach from the protrusion 26.

Once the archwire is received in the archwire-receiving region 44, the inherent resiliency of the clip 34 enables the arm portions 38 to spring back toward each other and toward their normal, relaxed or closed configuration as shown in FIGS. 1-4 and 6 in order to retain the archwire in the archwire slot 18. As shown for example in FIG. 2, the archwire receiving region 44 of the clip 34 is aligned with the archwire slot 18 when the clip 34 is assembled to the body 16. In the illustrated embodiment, the distance between the arm portions 38 in facial-lingual directions and on opposite sides of the archwire receiving region 44 is greater than the distance between the sidewalls 20, 22 of the archwire slot 18, which tends to reduce the resistance to sliding movement between the archwire and the appliance 10 that might otherwise be due to the clip 34.

The clip 34 (including the arm portions 38) is sufficiently stiff to retain the archwire in the archwire slot 18 during the course of treatment so long as the forces exerted by the archwire on the appliance 10 are below a certain minimum value in a direction opposite to the direction of insertion of the archwire into the archwire slot 18. However, whenever the forces exerted by the archwire on the appliance 10 in that same direction are greater than the minimum value, as might occur when unexpectedly high forces are encountered, the arm portions deflect outwardly and away from each other to open the clip 34 and release the archwire from the archwire slot 18. Further details regarding such forces are described in the aforementioned U.S. Pat. Nos. 6,302,688 and 6,582,226.

Preferably, the distal clip 36 is substantially identical to the mesial clip 34 and the distal protrusion 28 is substantially identical in mirror image to the mesial protrusion 26. The latch, comprising the clips 34, 36, preferably releases the archwire from the archwire slot 18 in a direction generally opposite to the direction of insertion of the archwire in the archwire slot 18 whenever the archwire exerts a force in that same direction on the appliance 10 that is in the range of about 0.2 lb (0.1 kg) to about 11 lb (5 kg), more preferably in the range of about 0.4 lb (0.2 kg) to about 5.5 lb (2.5 kg), and most preferably in the range of about 0.75 lb (0.34 kg) to about 3.0 lb (1.4 kg). Preferably, the minimum value is sufficiently high to prevent the archwire from unintentionally releasing from the archwire slot 18 during the normal course of orthodontic treatment. As such, the archwire can exert forces on the appliance 10 sufficient to carry out the treatment program and move the associated teeth as desired.

Preferably, the minimum value for self-release (i.e., self-opening) of the latch is substantially less than the force required in the same direction to debond the appliance 10 from the associated tooth. The minimum value for self-release of the latch is preferably less than about one-half of the force required in the same direction to debond the appliance 10 from the associated tooth. For example, if the expected bond strength of the adhesive bond between the appliance 10 and the associated tooth is 16 lbs (7.2 kg) in a direction generally opposite to the direction of insertion of the archwire in the archwire slot 18, the latch is constructed to self-release the archwire whenever the archwire exerts a force in that same direction on the appliance 10 that is somewhat greater than about 8 lbs (3.6 kg).

To determine the force to release the latch, a section of archwire is selected having an area in longitudinally transverse sections that is complemental to (i.e., substantially fills) the cross-sectional area of the archwire slot 18. Next, a sling is constructed and is connected to the archwire section at locations closely adjacent, but not in contact with the outer ends of the protrusions 26, 28. Optionally, the sling is welded or brazed to the archwire section. Next, the sling is pulled away from the appliance 10 in a direction opposite of the direction of insertion of the archwire into the archwire slot 18 while the appliance 10 is held in a stationary position, taking care to ensure that the longitudinal axis of the archwire section does not tip relative to the longitudinal axis of the archwire slot 18. The force to release the latch may be determined by use of an Instron testing apparatus connected to the sling, using a crosshead speed of 0.5 in/min (1.3 cm/min). Alternatively, a shaker apparatus (such as Model 300 from APS Dynamics of Carlsbad, Calif.) may be used along with a force transducer (such as model 208C01 from PCB of Buffalo, N.Y.) to measure the force.

Preferably, the distance between the opposed ends of the arm portions 38 is less than the overall occlusal-gingival dimension of the smallest archwire expected to be used during the course of treatment. The archwire need not fill the archwire slot 18 and flatly engage the wall portions defining the archwire slot 18 in all instances. For example, a somewhat smaller wire, and perhaps an archwire having a circular cross-sectional shape, may be used during a portion of the treatment program. The distance between the outer ends of the arm portions 38 is preferably selected so that a variety of archwires of different cross-sectional configurations may be used in connection with the appliance 10.

In this embodiment, and as mentioned above, the distal clip 36 is identical to the mesial clip 34. Optionally, however, it is possible to construct the clips 34, 36 somewhat differently to provide certain treatment procedures for a particular patient. For example, if a malpositioned tooth is initially oriented such that its mesial side should be rotated in a lingual direction in order to improve its position, it may be desirable to increase the stiffness of the mesial clip 34 so that a somewhat greater force is needed to release the archwire from the archwire slot 18 in comparison to the force needed to release the archwire from the distal clip 36. Other options are also possible.

Optionally, the spring clips 34, 36 are cut from a flat section of metallic stock material. Suitable metallic materials include shape memory alloys such as alloys of nitinol and beta-titanium. The clips 34, 36 may be cut from the stock material using a stamping, die cutting, chemical etching, EDM (electrical discharge machining), laser cutting or water jet cutting process. As another option, the clips 34, 36 could be formed and then heat-treated to set their shapes.

As presently preferred, the clips 34, 36 are made from flat annealed superelastic material (such as nitinol) having a pickled surface. Preferred nitinol materials have a nickel content of 55.97% by weight and an $A_f$ of 10°±5° C. The nitinol is cold worked to 37.5% and has a thickness in the range of about 0.012 in. (0.3 mm) to about 0.016 in. (0.4 mm). The clips 34, 36 are first cut in a rough cutting EDM process, then cut along their edges for an additional one or more times using an EDM process in order to smooth the edges. Alternatively, a laser cutting process or chemical etching process could be used to make the clips 34, 36. Preferably, the clips 34, 36 are constructed so that the longitudinal direction of the clip material, or the principal direction of grain flow of the clip material, is substantially parallel to the direction of extension of the arm portions 38 (i.e. in a generally occlusal direction in the illustrated embodiment).

Subsequent to the EDM, laser cutting or chemical etching process, the clips 34, 36 are tumbled in order to further round their edges. An example of a suitable tumbling machine is model LC-600-2+2 from Richwood Industries of Hawthorne, Calif. Using a small barrel, and a machine speed of 200 rpm, the clips are tumbled for about 2 hours in 500 cc of water and tumbling media. An example of suitable tumbling media is a mixture of 500 cc of ceramic media (shaped ACC, type M, size 3/16×3/8 (4.7 mm×9.5 mm)), 25 cc of white alumina powder no. 40, and 25 cc of soap powder compound no. 43, all from Richwood Industries. The tumbled clips are then polished for one-half hour in an ultrasonic screen barrel in a tank of solution. An example of a suitable solution is 3 liters of deionized water, 3 liters of pickling solution and 0.6 liter of hydrogen peroxide. A suitable pickling solution is No. TI121 Pickling Solution from Aya International of Los Angeles, Calif.

Although initially manufactured as separate, discrete components, the latch (comprising the clips 34, 36) and the archwire slot 18 together form an assembly that has a certain orientation relative to the base 12. This orientation is customized to the configuration of the specific tooth of the specific patient. In the illustrated embodiment, the clips 34, 36 and the archwire slot 18 have openings that are aligned with each other, and the orientation of the openings is custom-oriented to the orientation of the base 12. As a result, for any particular appliance (such as an appliance for an upper, right cuspid tooth), the orientation of the assembly may vary from patient to patient in accordance with the specific configuration of the patient's cuspid tooth and/or of other aspects of the dental structure for the specific patient undergoing treatment.

The body 16 includes a curved lingual wall section 50 and a curved facial wall section 52. The body 16 also includes a gingival wall section 54 that interconnects the wall sections 50, 52. Optionally, the gingival wall section 54 presents a somewhat flattened configuration. When viewed in directions along the longitudinal axis of the archwire slot 18, the wall sections 50, 52, 54 of the body 16 present a generally oval-shaped external profile that matches the generally oval-shaped external profile of the clips 34, 36. These oval-shaped profiles have a short axis and a long axis, and preferably the long axis is oriented in a direction that is perpendicular to the occlusal plane of the patient when the appliance 10 is bonded to the lingual side of the patient's tooth.

In addition, when the mesial clip 34 and the distal clip 36 are assembled to the body 16, the oval-shape external profile of the clips 34, 36 is aligned with the generally oval-shaped external profile of the body 16 with the result that a smoothly curved, compact assembly is presented. The matching, smoothly curved oval-shaped external profiles of the clips 34, 36 and the body 16 is highly beneficial in providing patient comfort, a particular advantage for appliances that are bonded to the lingual surfaces of a patient's teeth. Moreover, the openings of the clips 34, 36 are aligned with the opening of the body 16 that leads into the archwire slot 18.

Optionally, the appliance 10 includes a double ended or "T"-shaped hook 56 that extends outwardly from the lingual wall section 50 of the body 16. Other types of hooks are also possible, such as hooks with a generally "L"-shaped configuration, or hooks with ball-shaped heads. As yet another alternative, the appliance 10 may include a pair of spaced-apart "L"-shaped hooks with outer ends that extend in directions away from each other. The use of a pair of hooks is especially advantageous for appliances that have a relatively large width in a mesial-distal direction, such as appliances constructed for use on the patient's molar teeth. Although not shown in the drawings, the appliance 10 may also include tiewings in place of a hook or hooks or in addition to a hook or hooks.

Figure 7:
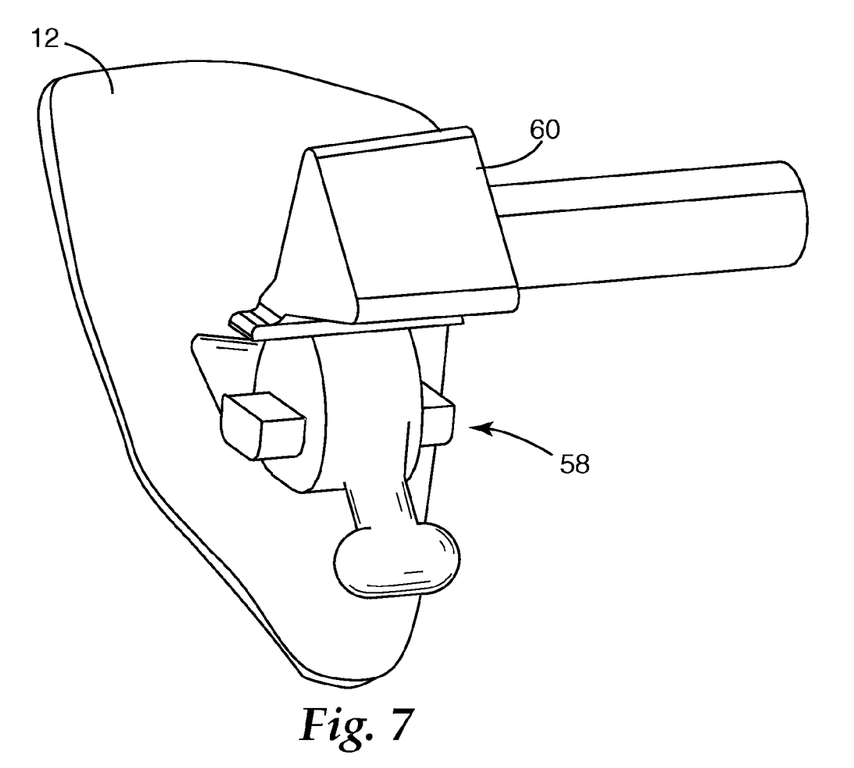
FIG. 7 is a perspective view of a preform used to make a body of the appliance shown in FIGS. 1-5, looking at the preform appliance in a direction toward its mesial, lingual and occlusal sides.

One method of making the appliance 10 includes the step of making an appliance preform such as the preform 58 illustrated in FIG. 7. The preform 58 initially includes a runner 60 which is detached when the archwire slot 18 is cut. Although certain features of the preform 58 as depicted in FIG. 7 are similar to features of the resulting appliance 10 shown in FIGS. 1-4, the preform 58 lacks the archwire slot 18. In addition, the protrusions 26, 28 of the resulting appliance 10 have a different configuration than the corresponding regions of the preform 58 shown in FIG. 7.

Optional methodologies for cutting the archwire slot 18 in the body 16 are described in published U.S. Patent Application 2007/0178423 (Rubbert et al.). As one example, a system for forming the archwire slot 18 may include an electrical discharge machining apparatus that includes a controller having memory which can provide for computer numerical control. The electrical discharge machining apparatus can include a traveling wire electrical discharge electrode, or a traveling wire electrode and a die-sinker electrical discharge electrode. The electrical discharge machining apparatus can include at least one drive section adapted to position the appliance 10 in electrical discharge contact with the electrode to form the archwire slot 18 and to simultaneously separate the body 16 from the runner 60 when forming the archwire slot 18 responsive to the control signal.

As the cutting tool (such as the electrical discharge machining apparatus) is advanced into the preform 58, the cutting tool also cuts a top portion of the protrusions 26, 28 to thereby form the top surfaces 30. Preferably, the bottom wall 24 of the archwire slot 18 is formed simultaneously with forming of the top surfaces 30. As one example, the preform 58 can be mounted on a drive table that is activated for movement by a control signal to enable a traveling wire electrode of an electrical discharge machining apparatus to simultaneously cut the bottom wall 24 and both of the top surfaces 30. Such a methodology helps ensure that the top surfaces 30 of the protrusions 26, 28 are each precisely coplanar with the bottom wall 24 of the archwire slot 18. This coplanar relationship is an advantage, in that the extended top surfaces 30 provide enhanced tipping control over movement of the associated tooth.

Optionally, an undercut 62 (see FIG. 1) is formed at the bottom of each sidewall 20, 22 of the archwire slot at a location next to the bottom wall 24. Optionally, the tabs 32 include facing wall surfaces with a configuration matching a portion of the undercuts 62 and aligned with the undercuts 62, as may occur when a traveling wire electrode as described above is used to form the archwire slot 18.

Figure 8:
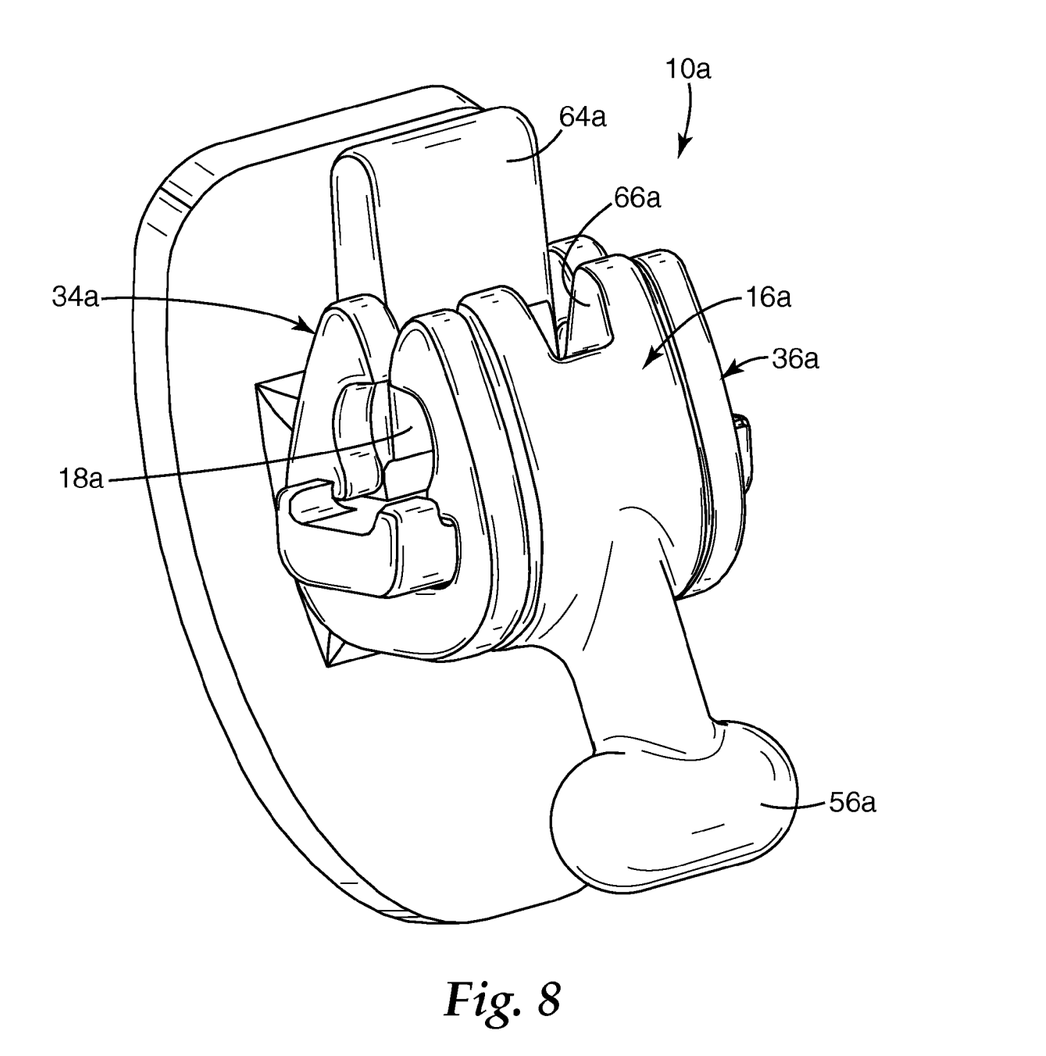
FIG. 8 is a perspective view of a self-ligating orthodontic appliance according to another embodiment of the present invention.
Figure 9:
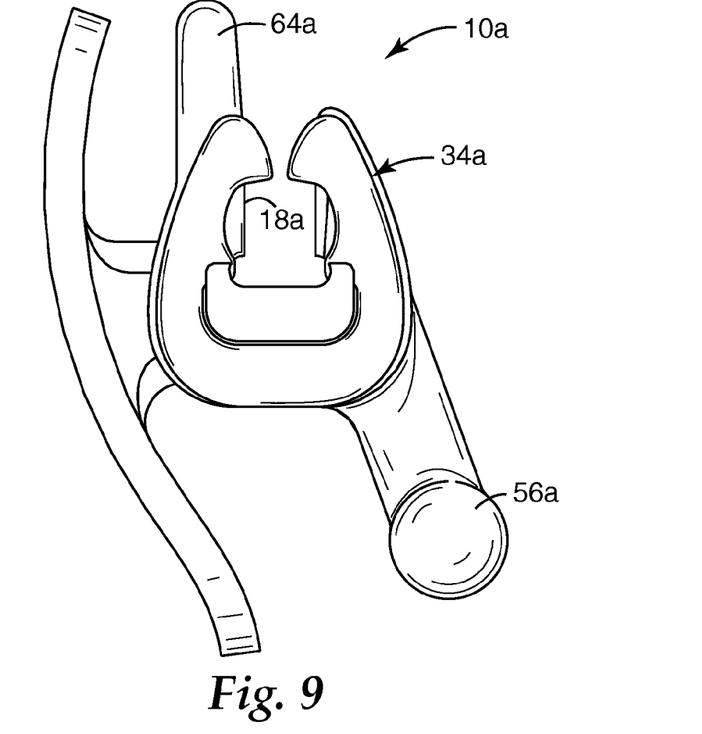
FIG. 9 is a side elevational view of the appliance shown in FIG. 8, looking in a direction that is aligned with the longitudinal axis of an archwire slot of the appliance.
Figure 10:
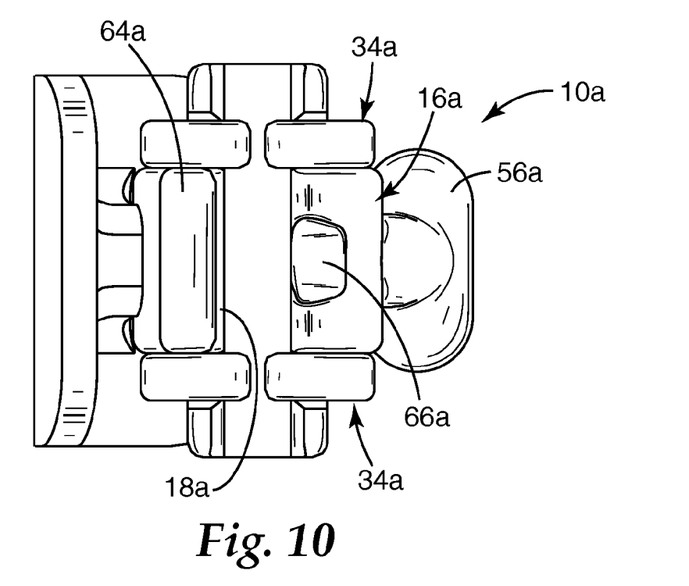
FIG. 10 is a top view of the appliance shown in FIGS. 8 and 9.

An orthodontic appliance 10a according to other embodiment of the invention is illustrated in FIGS. 8-10. Except as noted below, the appliance 10a is essentially the same as the appliance 10 and consequently a detailed description of the similar aspects will not be repeated.

The appliance 10a includes a body 16a with an archwire slot 18a that extends in a generally mesial-distal direction. A "T"-shaped hook 56a is integrally connected to the body 16a. The hook 56a extends in a generally gingival direction and is similar to the hook 56 described above. The appliance 10a also includes a hook 64a that extends in a generally occlusal direction. The hook 64a generally resembles a flat bar and is connected to the body 16a at a central location along the tooth-facing side of the archwire slot 18a.

Additionally, the body 16a includes a notch 66a that is adjacent to the opening to the archwire slot 18a and opposite the hook 64a. The notch 66a is adapted to receive a protrusion of a hand instrument that is constructed to remove an archwire from the archwire slot 18a. The notch 66a provides structure to facilitate steady and properly aligned contact of the hand instrument with the appliance 10a during a procedure to release the archwire from the appliance clips and remove the archwire from the archwire slot 18a. An example of a suitable hand instrument for removing the archwire is described in applicant's copending U.S. Patent Application Ser. No. 61/084,688 entitled "Hand Instrument for Removing an Orthodontic Archwire from an Orthodontic Appliance".

The appliance 10a also includes a pair of clips 34a, 36a that are coupled to the body 16a. The clips 34a, 36a have a generally "teardrop" external profile that matches a generally teardrop external profile of the body 16*a*. As with the oval-shaped external profiles mentioned above in connection with the appliance 10, the teardrop external profile of the appliance 10*a* presents a smoothly-curved external profile that is highly beneficial in provide patient comfort.

All of the patents and patent applications mentioned above are hereby expressly incorporated into the disclosure of this patent application. In addition, while the embodiments of the invention described above with particularity represent presently preferred embodiments, variations from those embodiments are possible without departure from the scope of the invention. Accordingly, the scope of the invention is to be determined by reference to the appended claims and their equivalents.

The invention claimed is:

1. A self-ligating orthodontic appliance comprising:
a base having an outer surface for bonding to a tooth;
a neck extending outwardly from the base;
a body connected to the neck, the body including an elongated archwire slot extending in a generally mesial-distal direction with two sidewalls and a bottom wall there between and facing an occlusal plane, and wherein the body includes a curved facial wall section, a curved lingual wall section, and a gingival wall section interconnecting the curved wall sections, the wall sections presenting an oval shaped or teardrop-shaped outline when viewed in directions along the longitudinal axis of the archwire slot and defining mesial and distal side surfaces; and
a first clip connected to the body for ligating an orthodontic archwire in the archwire slot, the clip including a curved facial arm portion, a curved lingual arm portion, and a bottom portion interconnecting the arm portions, the arm portions and bottom portion presenting an oval-shaped or teardrop-shaped outline that matches the outline of the side surfaces,
wherein the bottom section includes a portion residing beneath the bottom wall of the archwire slot, and wherein the outline of the clip is aligned with the outline of the body.

2. A self-ligating orthodontic appliance according to claim 1 wherein the body and the clip have oval-shaped outlines, and wherein the oval-shaped outlines include a short axis and a long axis, and wherein the long axis is oriented in a direction generally perpendicular to an occlusal plane.

3. A self-ligating orthodontic appliance according to claim 2 wherein the oval-shaped outline presented by the body and the oval-shaped outline presented by the clip include aligned openings for admitting an archwire in the archwire slot.

4. A self-ligating orthodontic appliance according to claim 3 wherein the aligned openings are located along the long axis.

5. A self-ligating orthodontic appliance according to claim 1 wherein the outer surface of the base has a configuration matching the configuration of a lingual tooth surface.

6. A self-ligating orthodontic appliance according to claim 1 wherein the neck extends along a reference plane generally parallel to an occlusal plane.

7. A custom, self-ligating orthodontic appliance comprising:
a base having a configuration matching the configuration of a specific tooth of a specific patient;
a body connected to the base, the body including an elongated archwire slot extending in a generally mesial-distal direction with two sidewalls and a bottom wall there between and facing an occlusal plane; and
a latch comprising a mesial clip and a distal clip coupled to the body for releasably retaining an archwire in the archwire slot, the latch and the body comprising initially separate, discrete components, wherein the body includes a curved lingual wall section and a curved labial wall section, the wall sections partially defining an oval-shaped or teardrop-shaped outline when viewed in directions along the longitudinal axis of the archwire slot and, each clip has an oval-shaped or teardrop-shaped outline that matches the outline of the body,
wherein the archwire slot and the latch together form an assembly, and wherein the assembly has a certain orientation relative to the base that is customized to the configuration of the specific tooth of the specific patient,
wherein each clip includes a curved lingual arm portion and a curved labial arm portion connected by a bottom section, and wherein the bottom section includes a portion residing beneath the bottom wall of the archwire slot, and wherein the curved arm portions match and are aligned with a least a portion of the curved wall sections.

8. A custom, self-ligating orthodontic appliance according to claim 7 wherein the archwire slot includes an opening, and wherein each clip has an opening that is aligned with the opening of the archwire slot.

9. A custom, self-ligating orthodontic appliance according to claim 8, and including a neck connecting the body to the base.

10. A self-ligating orthodontic appliance according to claim 1, wherein the neck has an overall height in the occlusal-gingival direction, connects the body to the base and extends between the body and the base in a generally facial-lingual direction, and wherein the base has overall dimensions in both an occlusal-gingival direction and a mesial-distal direction that are greater than the overall dimensions of the neck when viewed in reference planes perpendicular to the direction of extension of the neck away from the base.

11. A self-ligating orthodontic appliance according to claim 1, wherein the bottom wall is parallel to an occlusal plane of a patient when the bracket is located on a dental arch.

12. A self-ligating orthodontic appliance according to claim 1, and including a second clip, wherein the first clip comprises a mesial clip and the second clip comprises a distal clip.

13. A self-ligating orthodontic appliance according to claim 12, wherein each clip includes a first arm portion extending along a first one of the two sidewalls and a second arm portion extending along a second sidewall opposing the first sidewall, the first and second arm portions moveable away from each other to admit an archwire into the archwire slot.

14. A self-ligating orthodontic appliance according to claim 7, and wherein each clip includes a first arm portion extending along one of the two sidewalls and a second arm portion extending along a second sidewall opposing the first sidewall, the first and second arm portions moveable away from each other to admit an archwire into the archwire slot.

15. A self-ligating orthodontic appliance according to claim 1, wherein a first portion of the base extends in a gingival direction from the neck and a second portion of the base extends in an occlusal direction from the neck, such that the base has an overall height in both an occlusal-gingival direction and an overall width in mesial-distal direction that are both greater than the overall height and width of the neck when viewed in reference planes perpendicular to the direction of extension of the neck away from the base.

16. A self-ligating orthodontic appliance according to claim 9, wherein a first portion of the base extends in a gingival direction from the neck and a second portion of the base extends in an occlusal direction from the neck.

17. A self-ligating orthodontic appliance according to claim 1, and including a second clip, wherein the first clip comprises a mesial clip and the second clip comprises a distal clip, wherein the body includes the mesial and distal side surfaces each having the oval-shaped or teardrop-shaped outline when viewed in directions along the longitudinal axis of the archwire slot and each clip includes a face that matches at least a portion of and is aligned with a corresponding side surface of the body, each clip having the oval-shaped or teardrop-shaped outline that matches the outline of the corresponding side surface.

\* \* \* \* \*